US006899671B1

(12) United States Patent
Fontenot

(10) Patent No.: US 6,899,671 B1
(45) Date of Patent: May 31, 2005

(54) INTRAVAGINAL STIMULATION APPARATUS

(76) Inventor: Tony Fontenot, 1518 Jamie St., Mamou, LA (US) 70554

( * ) Notice: Subject to any disclaimer, the term of this patent is extended or adjusted under 35 U.S.C. 154(b) by 0 days.

(21) Appl. No.: 10/756,674

(22) Filed: Jan. 12, 2004

(51) Int. Cl.[7] .................................................. A61F 5/00
(52) U.S. Cl. ........................................................ 600/38
(58) Field of Search .......................... 600/38; 128/845; 482/51, 66, 92, 110, 114, 121, 122, 124, 131, 482/133

(56) References Cited

U.S. PATENT DOCUMENTS 5,851,175 A 12/1998 Nickell
6,152,865 A 11/2000 Beauvoir
6,203,491 B1 3/2001 Uribe
6,224,580 B1 5/2001 Christensen
6,254,561 B1 * 7/2001 Borden ........................ 602/24
6,422,993 B1 * 7/2002 Hudson ........................ 600/38
6,540,667 B2 * 4/2003 Hickman ..................... 600/38
6,579,228 B2 6/2003 Lien

* cited by examiner

*Primary Examiner*—John P. Lacyk
(74) *Attorney, Agent, or Firm*—Robert N. Montgomery

(57) ABSTRACT

A "Y" shaped tubular apparatus with each of the three arms of the apparatus containing a flexible member. The apparatus is both extendable in width and length with each arm rotatably adjustable and affixed at two ends with adjustable cuffs for securing the apparatus to the user at the ankles. One end of the extendable arm is capable of quick adaptation to a variety of intravaginal appliances.

In use, the apparatus is attached to the user's ankles via the adjustable cuffs, and is adjusted to the most comfortable position in a sitting or prone position. The user may then attach the intravaginal appliance of choice. Once insertion of the appliance is made, the user manipulates the apparatus by movement of the user's hips and buttocks in a natural rhythmic manner without the use of hands.

13 Claims, 3 Drawing Sheets

INTRAVAGINAL STIMULATION APPARATUS

FIELD OF THE INVENTION

This invention relates generally to sexual aids and more particularly to an apparatus to help achieve female sexual gratification through orgasm by artificial means.

GENERAL BACKGROUND

Throughout history women have sought sexual gratification by artificial means for a number of reasons. For example, sexual dysfunction between married partners may render conventional sex between partners impossible due to disease and resulting medications. Further, a great many women simply have no partners and do not wish to subject themselves to potential harm from strangers who may be disease carriers.

Conventional therapeutic devices currently available include various types of vibrators and sex aids. Many of these sex aids require the use of another partner, either male or female. Such aids also include electromechanical reciprocating devices that are mounted stationary using springs or elastic harnesses and the like. Such devices generally require unnatural positioning and are awkward to use at best. Many are simply artificial, hand held tools, such as plastic or rubber vibrators, that provide stimulation but fail to gratify a woman who wants not only the ultimate but also the feeling that she is actually having sex with a partner. Although there are some more complex devices that more closely resemble the male human anatomy, they have been found to be heavy, expensive, and require a great deal of manipulation and imagination to achieve any significant gratification. Therefore, a long-felt but unfilled need still exists in the art for a therapeutic apparatus that more closely resembles sexual intercourse and that can be used at any tempo, manner, or degree of gentleness or roughness, as desired, by the user in a natural position without the use of hand manipulation. The present invention solves many of the problems of the prior art while avoiding many of its shortcomings.

SUMMARY OF THE INVENTION

The present invention utilizes a "Y" shaped tubular apparatus with each of the three legs of the apparatus containing a flexible portion. The apparatus is extendable in length and affixed at two ends with adjustable cuffs for securing the apparatus to the user at the ankles. The third end is capable of adaptation to a variety of intravaginal appliances.

In use, the user simply attached the apparatus, via the adjustable cuffs, to the user's ankles and adjusts the length of the apparatus to the most comfortable position in a sitting or laying position, and attaches the intravaginal appliance of choice. Once insertion of the appliance is made, the user manipulates the apparatus by movement of the user's hips and buttocks in a natural rhythmic manner without the use of hands.

BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein.

DETAILED DESCRIPTION OF THE PREFERRED EMBODIMENT

Figure 1:
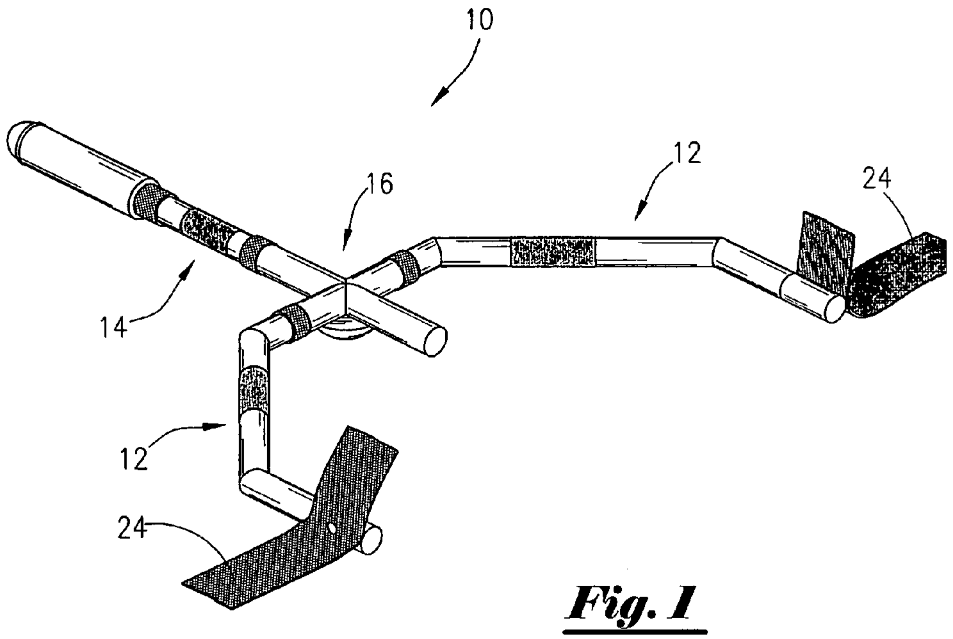
FIG. 1 is an isometric view of the preferred embodiment.
Figure 2:
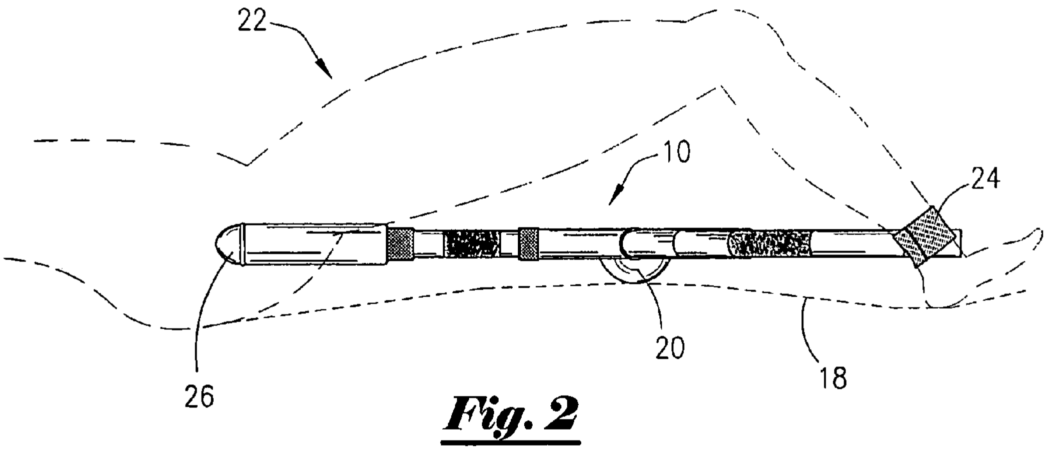
FIG. 2 is a side elevation view of the preferred embodiment in a position relative to a user.

The preferred embodiment of the assembled Intravaginal Stimulation Apparatus 10, as seen in FIG. 1, may be described as generally having a "Y" shaped configuration with two upper articulated arm assemblies 12 and an extendable arm assembly 14 rotatably and telescopically attached to a central cross assembly 16. In use the apparatus is placed on a surface 18 in a manner whereby the apparatus is pivotal about a hemispherical portion 20 located on one or both sides of the central cross assembly 16. The apparatus 10 is then attached to a user 22, in either the sitting or prone position, adjacent the user's ankles with the cuffs 24. The apparatus is then adjusted by extension or rotation of the extendable and/or articulated arms for comfort. Penetration is then made by inserting the appliance of choice such as item 26 attached to the apparatus as shown in FIG. 2 into the user's body cavity. Flexure of the user's legs, hips or buttocks allows for rhythmic movement of the apparatus 10 without use of the user's hands. Arm assemblies 12 & 14 are flexible to help to increase the range of motion and cuffs 24 are rotatable relative to the articulated arm assemblies 12 & 14.

Figure 3:
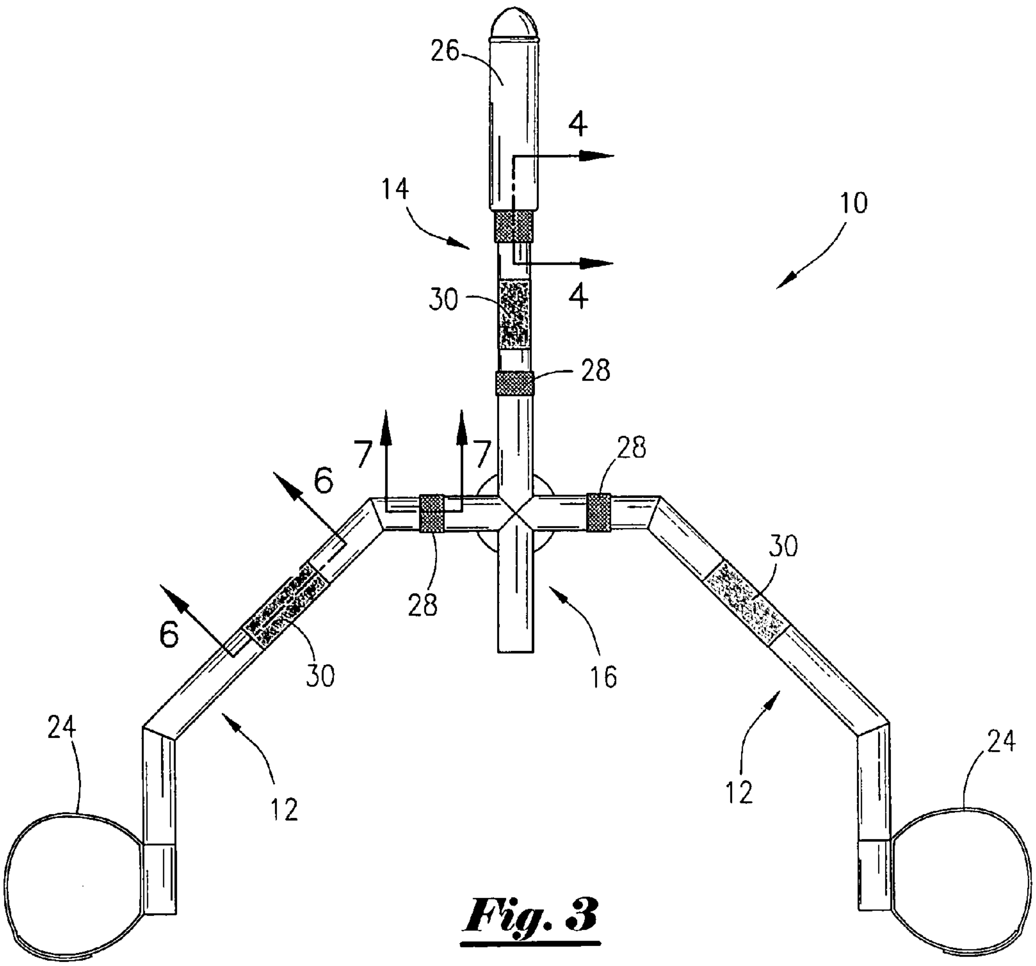
FIG. 3 is a top view of the preferred embodiment
Figure 3A:
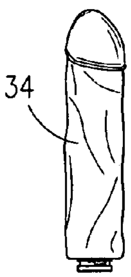
FIG. 3A is a side view of an alternative manipulator appliance.
Figure 3B:
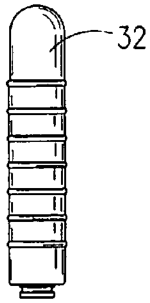
FIG. 3B is a side view of an alternative manipulator appliance.
Figure 4:
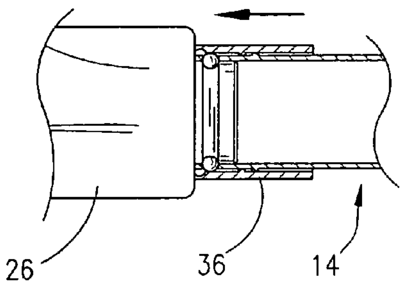
FIG. 4 is a partial cross section assembly view taken along sight line 4—4 seen in FIG. 3.
Figure 5:
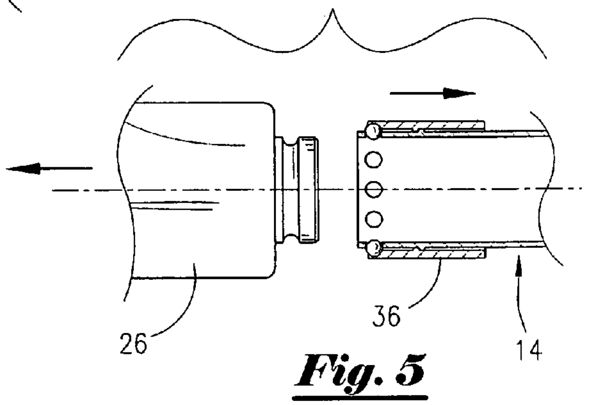
FIG. 5 is a partial cross section detached view taken along sight line 4—4 seen in FIG. 3.
Figure 6:
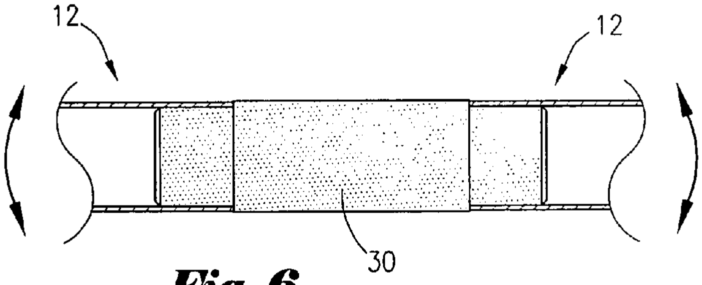
FIG. 6 is a partial cross section view taken along sight line 6—6 seen in FIG. 3.

Looking now at FIG. 3 the Intravaginal Stimulation Apparatus 10 is constructed of extremely lightweight materials such as aluminum, poly, or carbon fiber tubing and can be telescopically extended, rotated or readily disassembled by simply rotatably loosening the wedge lock fittings 28. Each of the articulated arm assemblies 12 may be constructed as shown in FIG. 3 with short sections of tubing joined at acute angles and having a flexible member 30 inserted therein for greater flexure of the articulated arm assemblies 12. Additional flexure may be gained by insertion of a flexible member 30 in the extendable arm assembly as well. The cuffs 24 may be padded or be a simple length of hook and latch material pivotally attached to the articulated arm assemblies 12. As further seen in FIGS. 3A and 3B a variety of appliances 32, 34 may be attached to the extendable arm assembly as desired by utilizing a quick-lock connection coupling such as illustrated in FIG. 4. Such locking devices are well known within the art. A portion of the quick-lock may be custom molded into the appliances 26, 32, and 34 for attachment as shown in FIG. 5. The flexible members 30 may be an elongated cylindrical piece of flexible urethane or simply a spring fitted longitudinally into each of the arm assemblies 12, 14.

Figure 7:
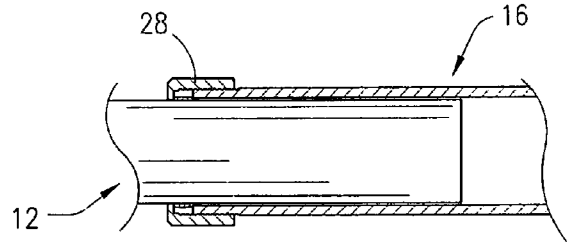
FIG. 7 is a partial cross section assembled view of the wedge lock taken along sight line 7—7 seen in FIG. 3.
Figure 8:
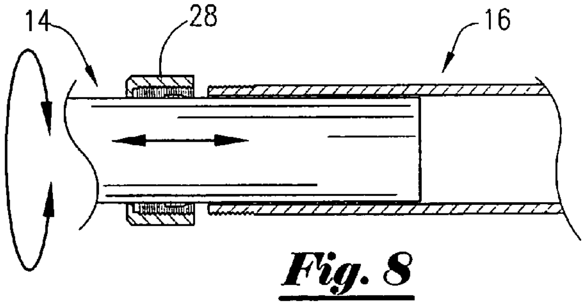
FIG. 8 is a partial cross section detached view of the wedge lock taken along sight line 7— 7 seen in FIG. 3.

Wedge lock threaded connectors 28, seen in FIGS. 7 and 8, are well known within the art and are quite useful for allowing slip and rotation of the tubular joints relative to the assemblies 12 and 14.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. An intravaginal stimulation apparatus comprising:

a) a "Y" shaped tubular assembly having two adjustable articulated arms and one extendable arm, each said articulated arm and said extendable arm further comprising a flexible member;

b) an adjustable cuff attached to an end of each said articulated arm;

c) a means for adjustably securing said articulated arms and said extendable arm; and d) an intravaginal appliance attached to an end of said extendable arm.

2. The intravaginal stimulation apparatus according to claim 1 wherein said apparatus further comprises a quick-lock means for interchanging said intravaginal appliance.

3. The intravaginal stimulation apparatus according to claim 1 wherein said extendable arm and articulated arms are telescopically retained by a cross assembly.

4. The intravaginal stimulation apparatus according to claim 1 wherein said adjustable cuff is rotatable relative to said articulated arm.

5. The intravaginal stimulation apparatus according to claim 3 wherein said cross assembly further comprises a means for infinitely securing said articulated arm and said extendable arm both rotationally and in telescopic extension relative to said cross assembly.

6. The intravaginal stimulation apparatus according to claim 2 wherein a portion of said quick-lock means is molded into said appliance.

7. The intravaginal stimulation apparatus according to claim 3 wherein said cross assembly further comprises a hemispherical portion adjacent at least one side.

8. The intravaginal stimulation apparatus according to claim 1 wherein said flexible member is a urethane member.

9. The intravaginal stimulation apparatus according to claim 1 wherein said flexible member is a spring.

10. A method of intravaginal stimulation comprising the steps of:

a) providing a "Y" shaped tubular assembly having two adjustable articulated arms and one extendable arm each said articulated arm and said extendable arm further comprising a flexible member, an adjustable cuff attached to an end of each articulated arm, a means for adjustably securing said articulated arms and an extendable arm and an intravaginal appliance attached to an end of said extendable arm;

b) attaching said assembly to a user by securing each said adjustable cuff to a user's ankle in a manner whereby said intravaginal appliance is readily insertable within the body of said user;

c) adjusting said articulated arms and said extendable arm for comfort; and d) utilizing a user's legs, hips, and buttocks to manipulate said "Y" shaped tubular assembly without the use of hands.

11. The method according to claim 10 further comprising the step of quickly exchanging one vaginal appliance for another through the use of a quick-lock coupling.

12. The method according to claim 10 further comprising the step of telescopically and rotatably securing said articulated and extendable arms with wedge lock fittings.

13. The method according to claim 10 further comprising the step of utilizing a hemispherical member centrally attached to said "Y" shaped tubular assembly to pivotally position and support said assembly during vaginal stimulation.

* * * * *